United States Patent
Salgo et al.

(10) Patent No.: US 6,824,517 B2
(45) Date of Patent: Nov. 30, 2004

(54) ULTRASOUND QUANTIFICATION IN REAL-TIME USING ACOUSTIC DATA IN MORE THAN TWO DIMENSIONS

(75) Inventors: Ivan S. Salgo, Andover, MA (US); Bernard J. Savord, Andover, MA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 45 days.

(21) Appl. No.: 10/179,361

(22) Filed: Jun. 25, 2002

(65) Prior Publication Data

US 2003/0236462 A1 Dec. 25, 2003

(51) Int. Cl.[7] ............................................... A61B 8/00
(52) U.S. Cl. ....................................... 600/443; 128/916
(58) Field of Search ............................ 600/437, 443, 600/447, 450, 454–456; 128/916; 382/128, 154, 173, 199, 256–259

(56) References Cited

U.S. PATENT DOCUMENTS

| | | | | |
|---|---|---|---|---|
| 4,159,462 A | * | 6/1979 | Rocha et al. .................. 367/97 |
| 4,737,921 A | * | 4/1988 | Goldwasser et al. ........ 364/518 |
| 5,195,521 A | * | 3/1993 | Melton, Jr. et al. ......... 600/447 |
| 5,322,067 A | * | 6/1994 | Prater et al. ................. 600/443 |
| 5,433,199 A | * | 7/1995 | Cline et al. .................. 600/443 |
| 5,435,310 A | * | 7/1995 | Sheehan et al. ............. 600/416 |
| 5,450,850 A | * | 9/1995 | Iinuma ......................... 600/455 |
| 5,465,721 A | * | 11/1995 | Kishimoto et al. .......... 600/443 |
| 5,476,096 A | * | 12/1995 | Olstad et al. ................ 600/443 |
| 5,846,200 A | * | 12/1998 | Schwartz ..................... 600/443 |
| 5,899,863 A | * | 5/1999 | Hatfield et al. ............. 600/443 |
| 5,903,664 A | * | 5/1999 | Hartley et al. .............. 382/154 |
| 5,924,991 A | * | 7/1999 | Hossack et al. ............. 600/443 |
| 6,031,935 A | * | 2/2000 | Kimmel ....................... 382/173 |
| 6,120,453 A | * | 9/2000 | Sharp .......................... 600/463 |
| 6,139,500 A | * | 10/2000 | Clark ........................... 600/443 |
| 6,217,520 B1 | * | 4/2001 | He et al. ..................... 600/467 |
| 6,346,124 B1 | * | 2/2002 | Geiser et al. ................ 600/450 |
| 6,385,332 B1 | * | 5/2002 | Zahalka et al. ............. 382/128 |
| 6,447,454 B1 | * | 9/2002 | Chenal et al. ............... 600/449 |
| 6,468,216 B1 | * | 10/2002 | Powers et al. .............. 600/443 |
| 6,537,220 B1 | * | 3/2003 | Friemel et al. .............. 600/447 |
| 6,545,678 B1 | * | 4/2003 | Ohazama ..................... 345/427 |
| 2002/0102023 A1 | * | 8/2002 | Yamauchi .................... 382/199 |

* cited by examiner

Primary Examiner—Francis J. Jaworski
(74) Attorney, Agent, or Firm—John Vodopia

(57) ABSTRACT

A system and method of ultrasound quantification acquires acoustic image data from anatomic locations distributed in more than 2 dimensions, and uses a segmentation algorithm to provide real-time volume measurements. A 2D array is used to acquire two orthogonal (bi-plane) 2D images simultaneously. The images are segmented individually to determine the volume borders using any number of acoustic algorithms. The borders from the two bi-plane images are mathematically combined to give a volume measurement. A control processor controls the system to thereby obtain instant feedback of the segmented image data and enhance the volume measurements of the image. The system and method is extended to a number of simultaneous 2D images and to a full 3D volume acquisition.

19 Claims, 2 Drawing Sheets

ULTRASOUND QUANTIFICATION IN REAL-TIME USING ACOUSTIC DATA IN MORE THAN TWO DIMENSIONS

BACKGROUND OF THE INVENTION

1. Field of the Invention

The present invention relates to an ultrasound quantification system acquiring acoustic image data from anatomic locations distributed in more than two dimensions, and using a segmentation algorithm to provide real-time volume measurements.

2. Description of the Related Art

Information as to a volume of a left ventricle of a heart as a function of time is useful to physicians in evaluating the heart. In particular, the volume at diastole, the volume at systole, the rate of change of the volume and other volume parameters, provide useful information to a physician.

Ultrasound imaging is an approach used to determine the volume of the left ventricle of the heart. The volume is determined from a two-dimensional ultrasound image by determining a cross-sectional area from the ultrasound image and making certain assumptions regarding a shape of the left ventricle.

FIG. 1 is a prior art diagram illustrating an ultrasound quantification system.

Referring now to FIG. 1, a scanner 20 performs ultrasound scanning of a specified region of patient's body, such as the heart. The scanner 20 includes an ultrasound transducer 10 for transmitting and receiving ultrasound energy. The transducer 10 transmits ultrasound energy into an image region and receives reflected ultrasound energy from organs within the patient's body.

As well known in the prior art, the transducer may include an array of transducer elements. By appropriately delaying the pulses applied to each transducer element, a focused ultrasound beam is transmitted along a desired scan line. A reflected ultrasound energy from a given point within the patient's body, is received by the transducer elements at different times. The transducer elements converge the ultrasound energy signals and supply the signals to a beam former. The beam former processes the signals and outputs a signal stream indicative of a focused received beam.

A depth and direction of a focal point of the received beam, relative to the ultrasound transducer, may be varied dynamically with time by appropriately delaying received signals from each of the transducer elements. The delayed signals from each of the transducer elements are summed to provide a scanner signal representative of a reflected energy level along a scan line. The above process is repeated for multiple scan lines to provide signals for generating an image of the prescribed region of the patient's body. Typically, the scan pattern is a sector scan wherein the scan lines originate at a point at a center of the ultrasound transducer and are directed at different angles.

An output of the scanner 20 is applied to a scan converter 30 which converts the sector scan information generated by the scanner 20 to a conventional raster scan display. An output of the scan converter 30 is then applied to an online display 40.

As indicated by a junction 35, ultrasound data output by the scan converter 30 is stored in the form of images on an optical disc 50. The optical disc 50 is a computer medium storage which may be a magnetic optical disc, JAZZ disc, ZIP disc, etc., or, for example, a network connection. The optical disc 50 is downloaded to a workstation 60. Here, segmentation 70 is applied which involves, for example, separating in cardiac applications, tissue from blood such that a pool of blood is segmented away from tissue data. An area or volume of the blood pool is thereby, quantified using a quantification technique 80. Thus, for example, a user may view the volume of blood in the left ventricle of the heart on an offline display 90.

It is clinically desirable to measure volumes of anatomic structures such as the left ventricle of the heart from ultrasound images. It is also desirable for these measurements to be performed semi-automatically by an ultrasound quantification system. Today these measurements are performed on one or more 2D images. If a single 2D image is used, the shape of the volume is assumed in the 3D dimension resulting in an erroneous result for asymmetric shapes. If multiple images are used, the multiple images are acquired at different times and transducer positions, and are neither time synchronous nor geometrically correct. Thus, obtained results are erroneous. Furthermore, all existing multi-plane solutions are not automatic and require manual tracing of the volume measurements.

Therefore, a need exists for a system capable of acquiring acoustic image data from anatomic locations distributed in more than two dimensions and using a segmentation algorithm to provide real-time volume measurements.

SUMMARY OF THE INVENTION

Accordingly, it is an object of the present invention to provide an ultrasound quantification system acquiring acoustic image data from anatomic locations distributed in more than two dimensions and using a segmentation algorithm to provide real-time volume measurements.

Objects of the present invention are achieved by providing an apparatus which includes a transducer acquiring image data from an image having more than two spatial dimensions. A segmentation device segments the image data to determine volume borders of the image data. The apparatus also includes a quantification device mathematically combining the volume borders of the image data to produce volume measurements in real-time.

Objects of the present invention are achieved by providing a method which includes acquiring acoustic image data from an image having more than two spatial dimensions. The method also includes segmenting the image data to determine volume borders of the image data, and combining the volume borders mathematically, to produce volume measurements in real-time.

Additional objects and advantages of the invention will be set forth in part in the description which follows, and, in part, will be obvious from the description, or may be learned by practice of the invention.

BRIEF DESCRIPTION OF THE DRAWINGS

These and other objects and advantages of the invention will become apparent and more readily appreciated from the following description of the preferred embodiment, taken in conjunction with the accompanying drawing of which.

DETAILED DESCRIPTION OF THE PREFERRED EMBODIMENTS

Figure 1:
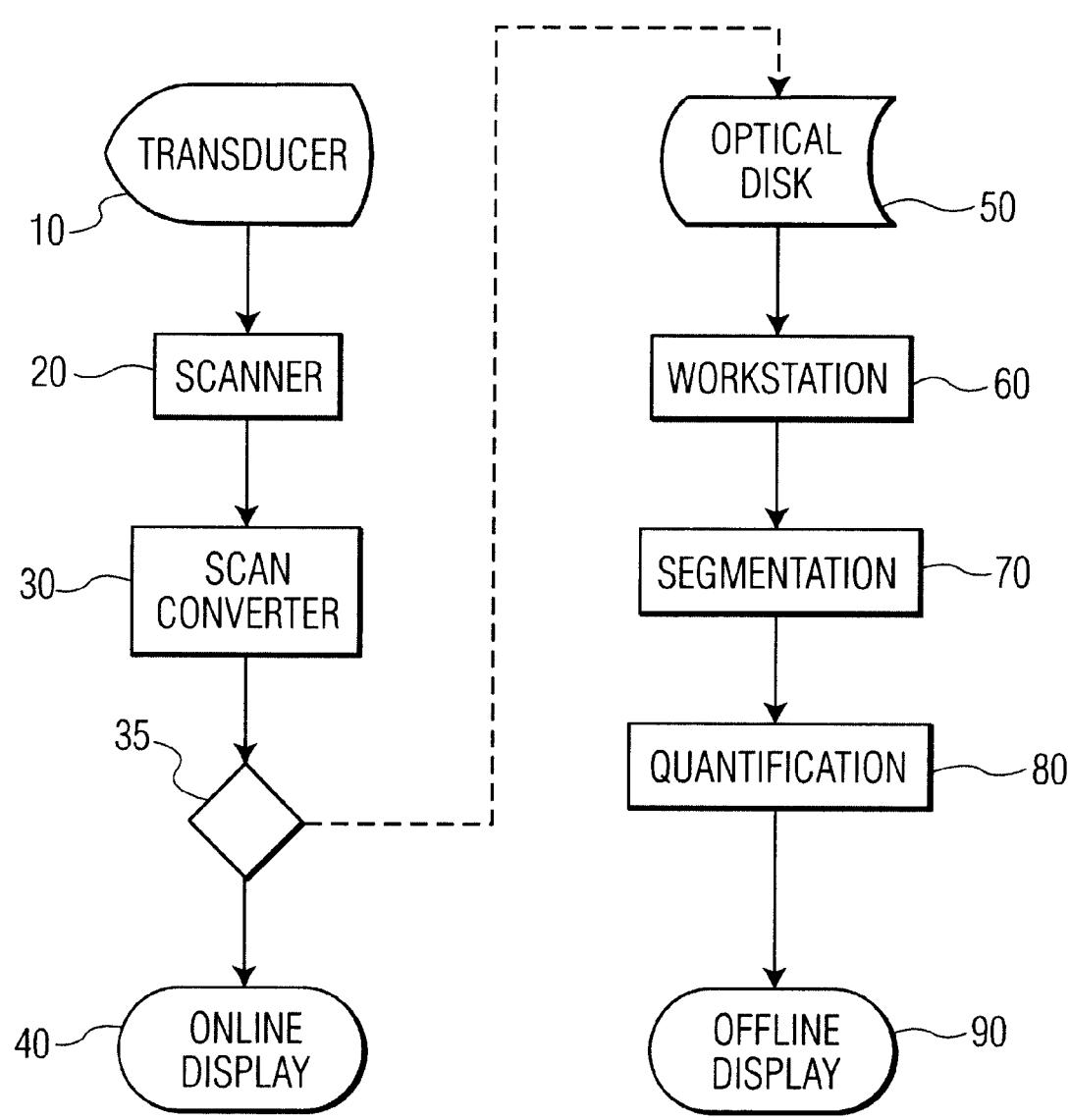
FIG. 1 is a prior art diagram illustrating an ultrasound quantification system.

Reference will now be made in detail to the present preferred embodiment of the present invention, examples of which are illustrated in the accompanying drawings, wherein like reference numerals refer to like elements throughout.

Figure 2:
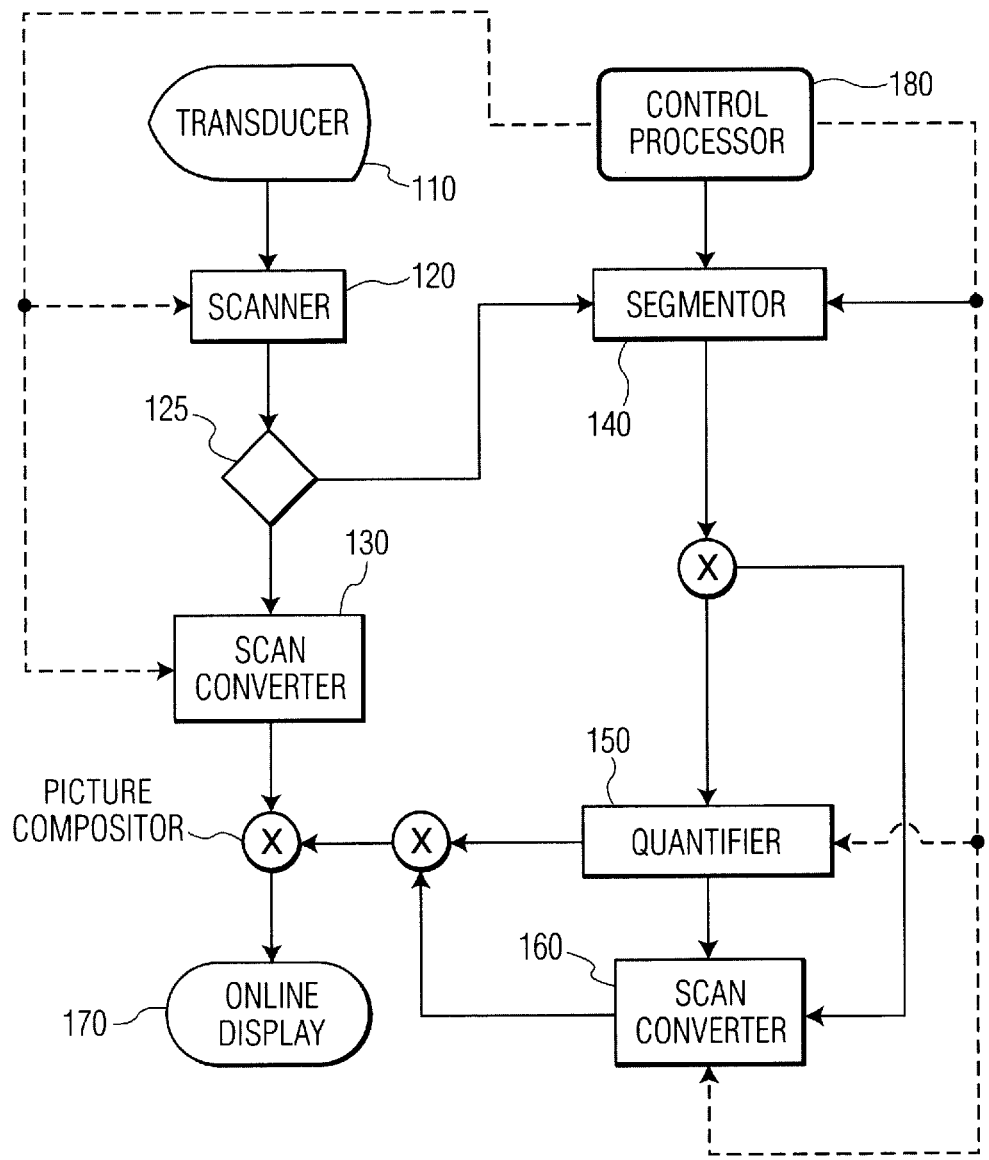
FIG. 2 is a diagram illustrating an ultrasound quantification system, according to an embodiment of the present invention.

FIG. 2 is a diagram illustrating an ultrasound quantification system, according to an embodiment of the present invention.

Referring now to FIG. 2, a scanner 120 performs ultrasound scanning of a specified region of patient's body, such as a left ventricle of a heart. The scanner 120 includes an ultrasound transducer 110 for transmitting and receiving ultrasound energy. The transducer 110 transmits ultrasound energy into an image region receives reflected ultrasound energy from organs within the patient's body. Data output by the scanner 120 is applied to a scan converter 130 which converts the data generated by the scanner 120 to a conventional raster scan display. An output of the scan converter 130 is then applied to an online display 170.

At a junction 125, the scanner 120 sends ultrasound data to a segmentor 140, automatically and on-line in a pre-scan conversion. The segmentor 140 performs, for example, segmentation of the ultrasound data on the left ventricle to determine volume borders of the left ventricle. After the ultrasound data is segmented, the segmented ultrasound data is output to a quantifier 150 and a scan converter 160. The quantifier 150 may be, for example, a SONO 5500. The quantifier 150 mathematically combines the volume borders of the left ventricle to give a volume measurement of the ultrasound data which is viewed on the online display 170. The scan converter 160 converts the ultrasound data such that an ultrasound image is viewed on an online display 170.

Also, in FIG. 2, a control processor 180 is used to control an operation of the scanner 120, scan converter 130, segmentor 140, quantifier 150, and scan converter 160. The control processor 180 controls various stages of image processing for instant feedback. For example, the control processor changes parameters or ultrasound properties in the segmentor 140 to enhance the volumetric borders of the ultrasound images.

Therefore, for example, the ultrasound quantification system acquires acoustic image data from anatomic locations distributed in more than two dimensions and uses a segmentation algorithm to provide real-time volume measurements. A 2D array is used to acquire two orthogonal (bi-plane) 2D images simultaneously. Then, the images are segmented individually to determine the volume borders using acoustic algorithms. The borders from the two bi-plane images are mathematically combined to give a volume measurement. The system and method may be extended to a number of simultaneous 2D images, or to a full 3D volume acquisition. Many different types of transducers may be used to acquire the images such as, for example, bi-plane transducers, wobblers, and rotating probes.

Various examples of an ultrasound quantification system are described herein. However, the present invention is not limited to these specific examples of the ultrasound quantification system.

Although a preferred embodiment of the present invention has been shown and described, it would be appreciated by those skilled in the art that changes may be made in these embodiments without departing from the principles and spirit of the invention, the scope of which is defined in the claims and their equivalents.

What is claimed is:

1. An apparatus comprising:
   a transducer acquiring image data from an image having more than two spatial dimensions;
   a segmentation device for automatically segmenting said image data to determine volume borders of an anatomical structure within the image data; and
   a quantification device mathematically combining the volume borders of said image data to produce volume measurements of the anatomical structure in real-time.

2. The apparatus according to claim 1, wherein said transducer acquires a full three-dimensional volume acquisition.

3. The apparatus according to claim 1, wherein said transducer acquires multiple two-dimensional planes.

4. The apparatus according to claim 1, further comprising:
   a control processor controlling said transducer, said segmentation device, and said quantification device to obtain instant feedback of the segmented image data, wherein parameters of the segmented image data are changed to enhance the volume measurement of the anatomical structure within the image.

5. The apparatus according to claim 1, wherein said transducer acquiring the image data is one of a 2D array, bi-plane transducer, wobbler, or a rotating probe.

6. The apparatus according to claim 1, wherein the segmentation device differentiates the volume borders between different types of image data.

7. The apparatus according to claim 1, wherein the real-time volume measurements are repeated at a rate of at least 10 Hz/s.

8. The apparatus as set forth in claim 1, further comprising an on-line display, wherein the volume measurements are displayed in real time.

9. The apparatus as set forth in claim 8, further comprising a scan converter for converting the image data to a conventional raster scan.

10. An apparatus comprising:
    acquisition means for acquiring image data from an image having more than two spatial dimensions;
    segmentation means for automatically segmenting said image data to determine volume borders of an anatomical structure included with the image data; and
    quantification means for combining the volume borders of said image data to produce volume measurements of the anatomical structure in real-time.

11. A method comprising:
    acquiring acoustic image data from an image having more than two spatial dimensions;
    segmenting said image data automatically to determine volume borders of an anatomical structure within the image data; and
    combining the volume borders mathematically, to produce volume measurements in real-time.

12. The method according to claim 11, wherein the image data acquired is a full three-dimensional volume acquisition.

13. The method according to claim 11, wherein the image data acquired are multiple two-dimensional planes.

14. The method according to claim 11, further comprising:
    obtaining instant feedback of the segmented image data; and
    changing parameters of the segmented image data to enhance the volume measurement of the image.

15. The method according to claim 11, wherein the image data is acquired by one of a 2D array, bi-plane transducer, wobbler, or a rotating probe.

16. The method according to claim 11, wherein said segmenting differentiates the volume borders between different types of image data.

17. The method according to claim 11, wherein the real-time volume measurements are repeated at a rate of at least 10 Hz/s.

18. The method as set forth in claim 11, further comprising a step of displaying the volume measurements in real time.

19. The method as set forth in claim 11, further comprising a step of converting the image data to a conventional raster scan in real time.

* * * * *